United States Patent [19]
Lee

[11] Patent Number: 5,780,048
[45] Date of Patent: Jul. 14, 1998

[54] FIRST AID BANDAGE DRESSING SYSTEM AND METHOD OF APPLICATION THEREOF

[76] Inventor: Chung Chih Lee, P.O. Box 196, Bellaine, Tex. 77402-0196

[21] Appl. No.: 822,272

[22] Filed: Mar. 20, 1997

[51] Int. Cl.$^6$ ............................................. A61F 13/00
[52] U.S. Cl. ...................................... 424/443; 424/448
[58] Field of Search ............................ 424/443, 448; 602/41

[56] References Cited

U.S. PATENT DOCUMENTS

| | | | |
|---|---|---|---|
| 4,245,630 | 1/1981 | Lloyd et al. | 128/155 |
| 4,552,802 | 11/1985 | Mechin | 428/255 |
| 4,784,653 | 11/1988 | Bolton et al. | 604/307 |
| 4,806,614 | 2/1989 | Matsuda et al. | 528/59 |
| 4,860,737 | 8/1989 | Lang et al. | 128/156 |
| 4,997,425 | 3/1991 | Shioya et al. | 604/304 |
| 5,192,536 | 3/1993 | Huprich | 424/78.08 |
| 5,254,132 | 10/1993 | Barley | 606/214 |
| 5,480,935 | 1/1996 | Greff | 524/776 |

*Primary Examiner*—D. Gabrielle Brouillette
*Attorney, Agent, or Firm*—Maryam Bani-Jamali

[57] ABSTRACT

This invention provides a first aid bandage dressing system and its method of application. The bandage dressing system is stored in an air-tight or vacuum package, consists of a number of layers including an uppermost layer and a bottommost layer and comprises a wound binding layer comprising one or more cyanoacrylates, a flexible layer that is positioned under the wound binding layer, a peelable cover that is positioned over the wound binding layer, an adhesive bandage that is the bottommost layer, a peelable covering that is the uppermost layer and a peelable attachment that is positioned over the adhesive bandage and that attaches a section of the adhesive bandage to the flexible layer and that attaches another section of the adhesive bandage to the peelable covering. Upon removal of the bandage dressing system from the air-tight or vacuum package, the peelable covering of the adhesive bandage and the peelable cover of the wound binding layer are removed. The wound binding layer is then positioned on the wound and the sections of the adhesive bandage that are attached to the peelable covering are then secured to the sides of the wound until a water tight seal is formed over the wound. Upon formation of the water tight seal, the adhesive bandage is either removed as one piece or washed away gradually in portions. The flexible layer of the wound binding layer keeps the wound dry and water proof. After the majority of the initial wound healing phase has taken place, the wound binding layer and the flexible layer of the bandage dressing system slough off naturally and gradually from the wound or can be peeled off if desired. In another embodiment of the present invention, the peelable covering, the peelable attachment and the adhesive bandage are excluded from the marketed first aid bandage dressing system. Thus, there is no need for removal of the peelable covering before application of the bandage dressing system to the wound, for attachment of the adhesive bandage to the wound site and for removal of the adhesive bandage upon formation of a water-tight seal.

31 Claims, 4 Drawing Sheets

FIRST AID BANDAGE DRESSING SYSTEM AND METHOD OF APPLICATION THEREOF

BACKGROUND OF THE INVENTION

1. Field of the Invention

This invention relates to a first aid bandage dressing system positioned in an air-tight or vacuum package and comprising several peelable layers, a flexible layer and a wound binding layer comprising cyanoacrylate and other chemical ingredients. The method of application of the bandage dressing system and the method of treating wounds by applying the first aid bandage dressing system are also described.

2. Description of the Prior Art

A wide variety of first aid bandage systems and of wound dressings have been developed within the past few decades. Attempts have been made to develop bandages which are self-adhesive and sterile. Many of the existing bandage systems and wound dressings have a unique method of application and comprise specialty chemical compositions for coating wounds. New methods for treating wounds have evolved upon application of these bandage systems and wound dressings.

Novel constructions of first aid bandage systems are protected by a group of patents. The new features of these bandage systems rest in the construction of and in the combined operation of the physical parts of the bandage system, rather than in chemical compositions used with or within the bandage systems for coating and healing the wound. One such bandage system, which is considerably closer in construction to the application than other patented inventions, is protected in Lloyd et al., issued on Jan. 20, 1981, U.S. Pat. No. 4,245,630. Lloyd et al. patent a tearable composite multi-layered strip of materials comprising a backing layer, an adhesive layer on an internal surface of the backing layer, an absorbent layer on the adhesive layer and a removable protective layer that is peelably adherent to exposed margins of the adhesive layer. At least one layer is finger-tearable from any point along its length in a predetermined transverse direction. The constructions protected by hundreds of comparable bandage system patents have been reviewed. However, none of the bandage systems has a construction that is similar to the first aid bandage dressing system of applicant.

A group of first aid bandage systems and wound dressings concentrates mostly on composition, physical and/or chemical, of the components of the various "physical parts" of the patented invention. This category does not emphasize the composition of the components having direct medical and healing properties, although the holders of the medicaments are often claimed. In U.S. Pat. No. 4,860,737, issued on Aug. 29, 1989, Lang et al. introduce a wound dressing comprising a wound facing layer having a conformable net of elastomer, an intermediate absorbent layer having a conformable open cell foam of hydrophilic polymer and an outer layer having a conformable microporous film.

Shioya et al., U.S. Pat. No. 4,997,425, issued on Mar. 5, 1991, patent a wound dressing with a porous layer structure comprising a first layer, with pores of about 20 to 500 μm in diameter and a thickness of about 1 to 10 mm, and a second layer, with pores of not more than about 20 μm in diameter and a thickness of about 0.5 to 5 μm, which are continuously formed by quenching and freeze drying a solution of a polyamino acid under vacuum.

Mechin, issued on Nov. 12, 1985, U.S. Pat. No. 4,552,802, patents a self-adhesive product applicable as a dressing and in the form of a sheet, band or tape comprising a cellular support coated with at least one layer of synthetic or natural elastomer.

The present application covers the physical characteristics and the chemical composition of the various "physical parts" of the bandage system. The physical parts of the bandage dressing system are combinedly important in setting up the bandage system of the applicant.

In a group of patents protecting wound dressings and bandage systems, the application of novel chemical compositions for medical and healing purposes, versus chemicals used in the construction of the various "physical parts", is claimed. The chemical composition of the medication, which is often used with or within the bandage system and with or within the wound dressing for coating and healing the wound, and the structure and function of the holders of the medication present some new features.

Matsuda et al., U.S. Pat. No. 4,806,614, issued on Feb. 21, 1989, patent an application of a surgical adhesive, comprising either an NCO-terminated hydrophilic urethane prepolymer derived from hydrophilic polyether polyol of higher oxyethylene content or a combination of the urethane prepolymer with unsaturated cyano compound containing a cyano group attached to a carbon atom constituting the polymerizable double bond, for surgical bonding of tissue.

Bolton et al., U.S. Pat. No. 4,784,653, issued on Nov. 15, 1988, patent an absorbent adhesive dressing that has a three layer sandwich-type construction with an occlusive film as the outer layer, an absorbent layer of fibers as the middle layer and a wet-stick adhesive as the inner wound facing adhesive layer having a porosity of less than 0.5 cc/sec/in$^2$ and comprising a mixture of N-vinyl caprolactam and n-butyl acrylate or 2-ethylhexyl acrylate or a combination thereof.

Many other similar chemical-composition oriented patents concentrating on composition of wound dressings have been studied. The wound dressing of the present application comprises, among other chemicals, cyanoacrylate and derivatives of cyanoacrylates and has a chemical composition that is both novel and non-obvious to a person skilled in the related art.

A relatively small group of patents related to the present invention introduces combinedly novelties in the construction of bandage systems and in wound dressings used with or within the bandage systems for coating and healing the wound. The combination of new, nonobvious features in the construction of the bandage system and in wound dressings used with or within the bandage systems (said combination being referred to hereafter as the bandage dressing system) establishes an essential advantage of the present application. In the past few decades, there has also been some focus on methods of coating wounds. Huprich, U.S. Pat. No. 5,192,536, registered on Mar. 9, 1993, discusses a method and composition for coating a wound with polyether polyurethane solution, consisting of about 20 percent by weight of polyether polyurethane resin pellets dissolved in about 80 percent by weight of tetrahydrofuran, which dries to form a nonfibrous film for promoting healing. The method of treating wounds that exists in the present application is not discussed in any registered patent and has not been known to any person skilled in the related art.

The above-listed patents and many other similar inventions have been developed, some of which still exist in the market. The patents and innovations in the market have been usually oriented either towards first aid bandage systems or towards wound dressings. Both the chemical composition and physical characteristics are of principle importance with respect to this novel bandage dressing system. Few of the previous and existing innovations have presented bandage systems that, along with some wound dressing, could perform the functions that are unique to the present invention. This invention not only strives towards presenting a unique bandage dressing system, but also provides a bandage system, as well as a wound dressing, that is each new and nonobvious. Even further, the method of application of the bandage system and of the bandage dressing system are novel. In addition, this invention introduces a new method of treating wounds.

SUMMARY OF THE INVENTION

A primary object of the invention is to devise a bandage dressing system which improves healing process of a wound and creates a water-proof barrier which prevents contamination and infection of the wound.

Another object of this invention is to devise a bandage dressing system which can be positioned quickly and easily on the wound, without the need to use any accessory or third-party assistance.

Still another object of this invention is to devise a bandage dressing system which eliminates the necessity of changing of or removing wound binding layers.

Yet another object of this invention is to devise a bandage dressing system which is flexible so that it will readily conform to the contours of the wound site.

An additional object of this invention is to devise a bandage dressing system which does not require the patient to remain in any particular positions for an extended period of time merely to allow a barrier wound binding layer to set-up or to cure.

Another object of this invention is to devise a bandage dressing system which can be applied directly to the site of the wound without requiring oral administration.

Yet another object of this invention is to devise a bandage dressing system which is self-adhesive.

An additional object of this invention is to devise a bandage dressing system which seals the wound and minimizes contact between the external environment and the wound during its initial phase of healing.

Another object of this invention is to devise a bandage dressing system which is physiologically acceptable and biologically compatible to the human tissue.

A final object of this invention is to devise a bandage dressing system which is not painful to remove.

Additional objects and advantages of the invention will be set forth in part in a detailed description which follows, and in part will be obvious from the description, or may be learned by practice of the invention.

The present invention provides a first aid bandage dressing system and the method of application of the bandage dressing system. The bandage dressing system is stored in an air-tight or vacuum package, consists of a number of layers including an uppermost layer and a bottommost layer and comprises a wound binding layer comprising one or more cyanoacrylates, a flexible layer that is positioned under the wound binding layer, a peelable cover that is positioned over the wound binding layer, an adhesive bandage that is the bottommost layer, a peelable covering that is the uppermost layer and a peelable attachment that is positioned over the adhesive bandage and that attaches a section of the adhesive bandage to the flexible layer and that attaches another section of the adhesive bandage to the peelable covering.

Upon removal of the bandage dressing system from the air-tight or vacuum package, the peelable covering of the adhesive bandage and the peelable cover of the wound binding layer are removed. The wound binding layer is then positioned on the wound and the sections of the adhesive bandage that are attached to the peelable covering are then secured to the sides of the wound until a water tight seal is formed over the wound. Upon formation of the water tight seal, the adhesive bandage is either removed as one piece or washed away gradually in portions. The flexible layer of the wound binding layer keeps the wound dry and water proof. After the majority of the initial wound healing phase has taken place, the wound binding layer and the flexible layer of the bandage dressing system slough off naturally and gradually from the wound or can be peeled off if desired.

In another embodiment of the present invention, the peelable covering, the peelable attachment and the adhesive bandage are excluded from the marketed first aid bandage dressing system. Thus, there is no need for removal of the peelable covering before application of the bandage dressing system to the wound, for attachment of the adhesive bandage to the wound site and for removal of the adhesive bandage upon formation of a water-tight seal.

It is to be understood that the descriptions of this invention are exemplary and explanatory, but are not restrictive, of the invention. Other objects and advantages of this invention will become apparent from the following specification and from any accompanying charts, tables, examples and drawings.

BRIEF DESCRIPTION OF CHARTS, TABLES, EXAMPLES AND DRAWINGS

Any accompanying charts, tables, examples and drawings which are incorporated in and constitute a part of this specification, illustrate examples of preferred embodiments of the invention and, along with the description, serve to explain the principles of the invention.

Due to the thinness and sizes of the layers of the bandage dressing system and due to the difficulty in showing some layers in proportion to the other layers, the incorporated drawings may not indicate exact ratios in measurement among different components of the drawings. However, the figures accurately represent the construction of the bandage dressing system.

DETAILED DESCRIPTION OF THE PREFERRED EMBODIMENT

Preferred embodiments of the present invention are illustrated in any charts, tables, examples and drawings that are included.

The present invention provides a first aid bandage dressing system 10 and the method of application of the bandage dressing system 10. In addition, the method of treating wounds by applying the first aid bandage dressing system 10 is presented.

Figure 1:
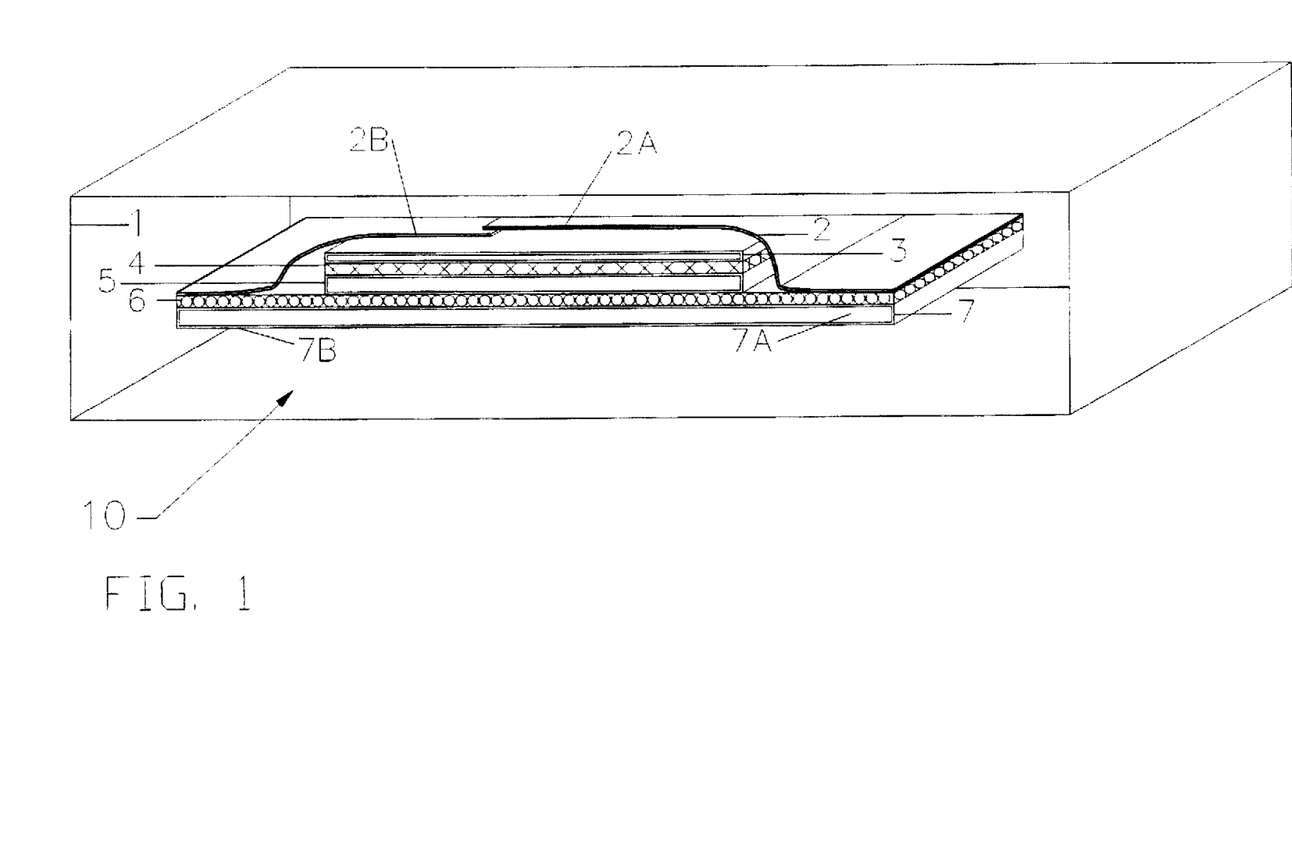
FIG. 1 shows an enlarged, perspective view of a version of a first aid bandage dressing system contained within an air-tight or vacuum package.
Figure 2:
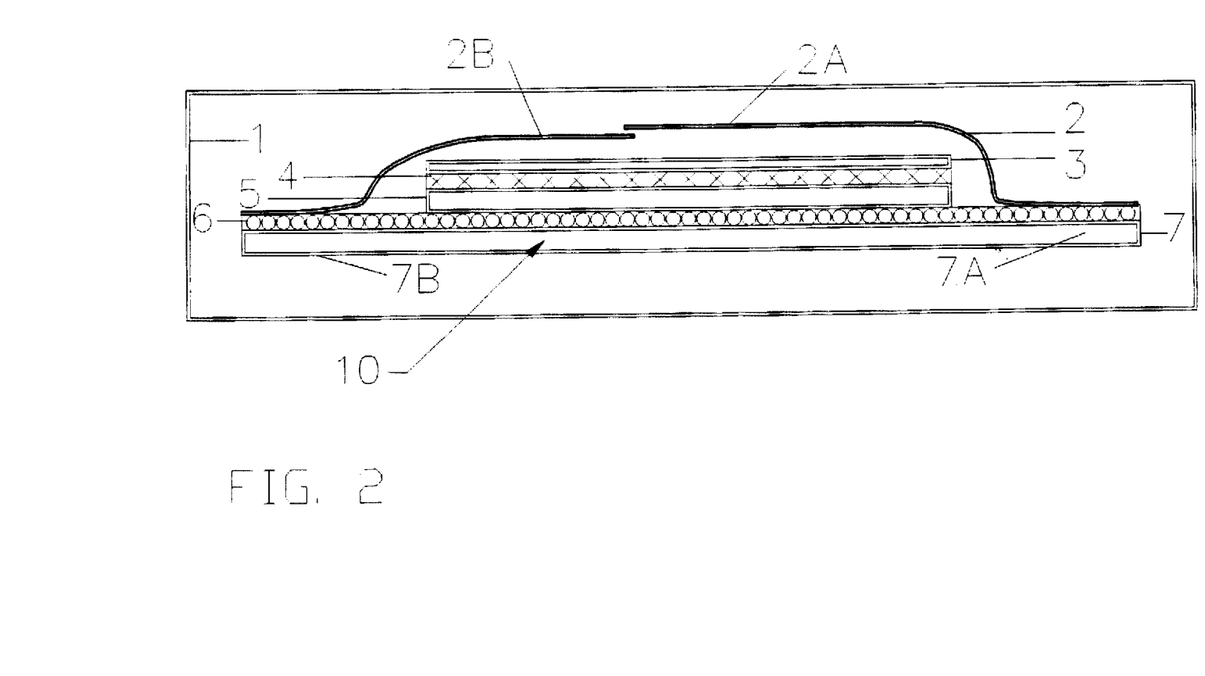
FIG. 2 shows a cross-sectional view of the bandage dressing system of FIG. 1.

As shown in FIG. 1 and FIG. 2, the bandage dressing system 10 is stored in an air-tight or vacuum package 1 and comprises a wound binding layer 4, a flexible layer 5 that is positioned under the wound binding layer 4, a peelable cover 3 that is positioned over the wound binding layer 4, an adhesive bandage 7 that is the bottommost layer, a peelable covering 2 that is the uppermost layer and a peelable attachment 6 that is positioned over the adhesive bandage 7. A portion of the peelable attachment 6 attaches the flexible layer 5 to a section of the adhesive bandage 7 and another portion of the peelable attachment 6 attaches the peelable covering 2 to another section 7A,7B of the adhesive bandage 7. The components of the bandage dressing system 10 are arranged basically in layers.

In a most preferred embodiment, when the bandage dressing system 10 is laid and spread out horizontally on a surface, the adhesive bandage 7 is the bottommost layer and the peelable covering 2 serves as the uppermost layer. The peelable cover 3 of the wound binding layer 4 is positioned between the peelable covering 2 and the wound binding layer 4. The wound binding layer 4 lies below the peelable cover 3 and above the flexible layer 5 which in turn lies under the wound binding layer 4. The flexible layer 5 is positioned between the wound binding layer 4 and the peelable attachment 6. The adhesive bandage 7 and the peelable covering 2 establish the boundaries for the peelable cover 3, the wound binding layer 4, the flexible layer 5 and the peelable attachment 6. With the peelable attachment 6 attaching the flexible layer 5 to the adhesive bandage 7 and attaching the peelable covering 2 to the adhesive bandage 7, all layers of the bandage dressing system 10 are attached to at least one other layer. Thus, the bandage dressing system 10 is presented in the market as one unit and, to the consumer, probably resembles to a certain extent presently-marketed bandage dressing systems such as BAND-AID®.

Figure 3:
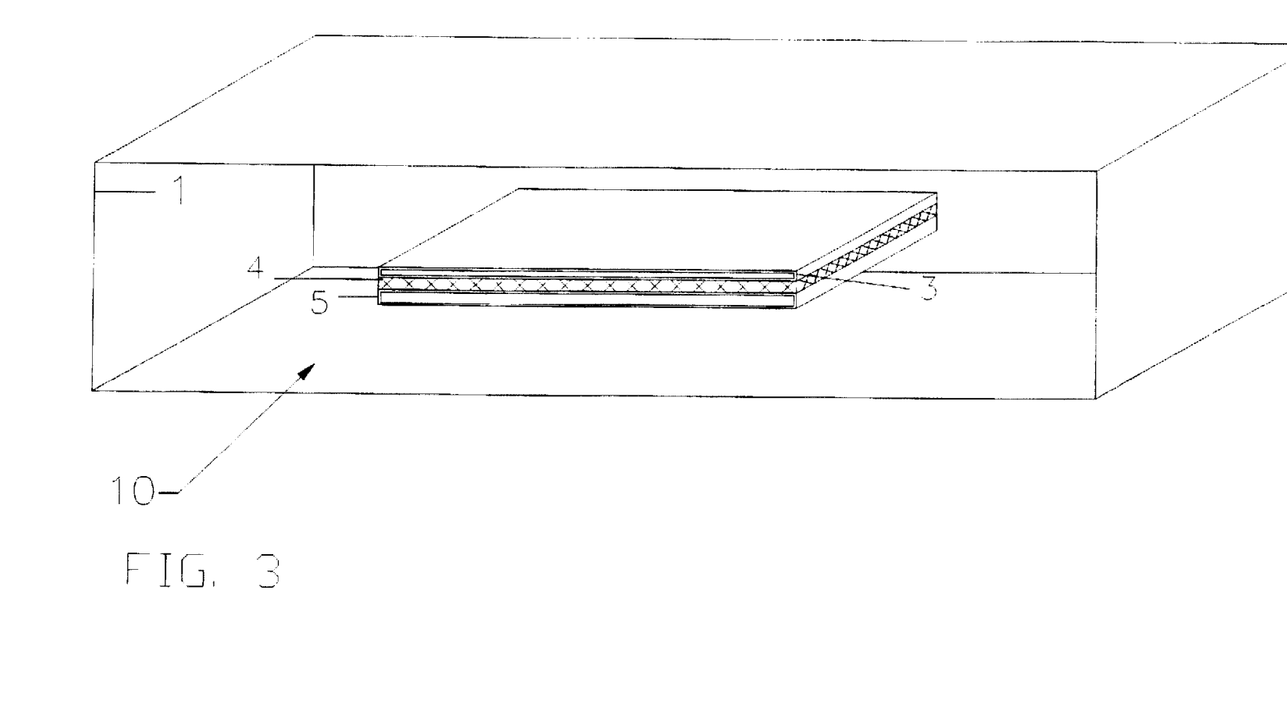
FIG. 3 shows an enlarged, perspective view of a version of a first aid bandage dressing system contained within an air-tight or vacuum package.
Figure 4:
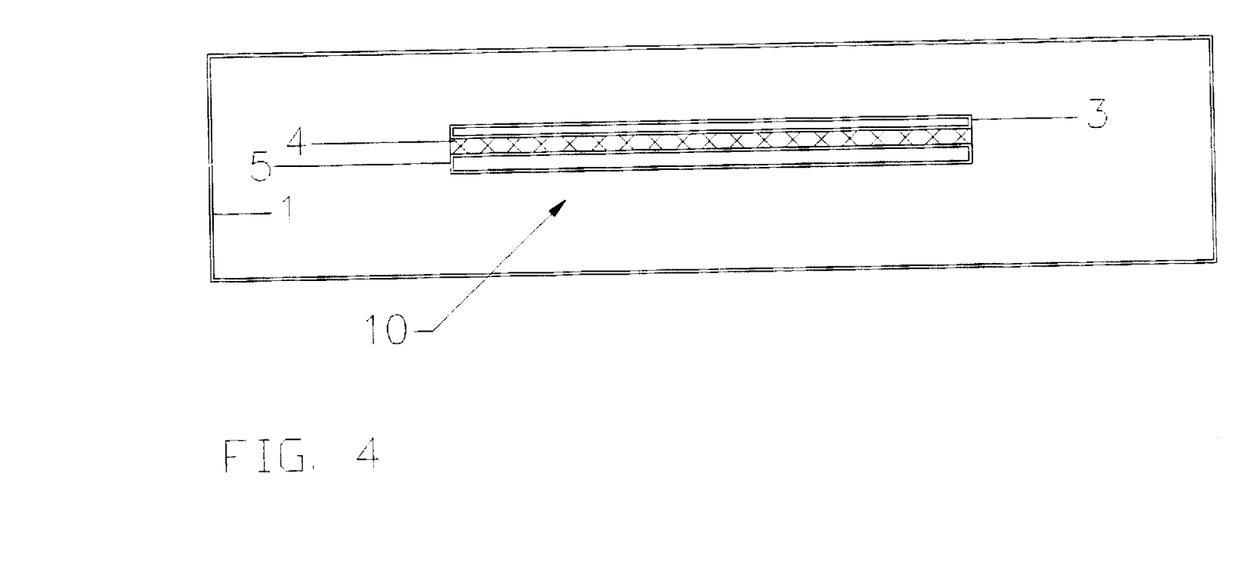
FIG. 4 shows a cross-sectional view of the bandage dressing system of FIG. 3.

The flexible layer 5 and the wound binding layer 4, which jointly provide a barrier for the wound against contamination and external moisture, play an essential role in the application of the bandage dressing system 10. In a marketable embodiment of the first aid bandage dressing system 10, the adhesive bandage 7, the peelable attachment 6 and the peelable covering 2 are not included. The wound binding layer 4 and the flexible layer 5 are applied to the wound site without the adhesive bandage 7 and are the sole components of the first aid bandage dressing system 10 that are positioned on the wound. (Please refer to FIG. 3 and FIG. 4.) The results obtained from the application of the bandage dressing system 10 are not effected if the adhesive bandage 7, the peelable attachment 6 and the peelable covering 2 are not included as components of the marketed product. The deletion of the adhesive bandage 7, the peelable attachment 6 and the peelable covering 2 from origin when the bandage dressing system 10 is in the vacuum or air-tight package 1 has no negative effect on the performance of the bandage dressing system 10. The deletion of a need for removing an adhesive bandage 7 that has been attached to the skin avoids the pain and discomfort accompanying the removal of a version of the adhesive bandage 7 that is not removed by dissolving during washing. Deletion of such adhesive bandage 7 from the bandage dressing system 10 provides a more preferred embodiment for wounds that are positioned in locations of the body with longer or more abundant hair. The exclusion of such adhesive bandage 7, from components of the bandage dressing system 10 that are applied to the wound, deletes the inconvenience and discomfort of removing the adhesive bandage 7 from the wound after the flexible layer 5 and the wound binding layer 4 are cured to the wound.

The inclusion of the adhesive bandage 7, the peelable attachment 6 and the peelable covering 2 may provide a more user-friendly product. Consumers may be more attracted to a product that resembles bandage dressing systems that are already available in the market. Upon development of some familiarity of consumers with the present invention, other versions of the bandage dressing system 10 may be marketable.

The present application concentrates on the first embodiment of the bandage dressing system 10 that includes the peelable covering 2, the adhesive bandage 7 and the peelable attachment 6. The features and application of the second embodiment of the bandage dressing system 10 correspond to the features and application of the first embodiment, except that the peelable covering 2, the adhesive bandage 7 and the peelable attachment 6 are not included. In the second embodiment, the vacuum or air-tight package 1, the peelable cover 3, the wound binding layer 4 and the flexible layer 5 have the same features and application that they have in the first embodiment. Therefore, the second embodiment of the bandage dressing system 10 is not individually described. It also should be emphasized that other versions of the first aid bandage dressing system 10 may be developed in the future. However, the other versions will closely relate to these two embodiments such that the included modifications and changes will fall within the scope of the present invention.

In a preferred embodiment, the bandage dressing system 10 comprises, by weight:

| COMPONENT OF BANDAGE DRESSING SYSTEM 10 | APPROXIMATE RANGE OF PERCENTAGE OF TOTAL WEIGHT |
|---|---|
| peelable covering 2 of adhesive bandage 7 | 3% to 20% |
| peelable cover 3 of wound binding layer 4 | 1% to 15% |
| wound binding layer 4 | 2% to 20% |
| flexible layer 5 | 5% to 50% |
| peelable attachment 6 | 1% to 5% |
| adhesive bandage 7 | 20% to 70% |

Each component plays a specific and particular role in the application of the bandage dressing system 10. However, the importance of the role played by each component is not proportional to the percentage, whether by weight or volume, of the bandage dressing system 10 assigned to that component. The air-tight or vacuum package 1 is used in order to prevent contact of the wound binding layer 4 with moisture and oxygen in the air and to avoid premature curing of the wound binding layer 4 prior to its application to the wound. The air-tight or vacuum package 1 is preferably made up of aluminum, paper polyethylene or any other suitable material.

As in many presently-marketed bandage dressing systems, the peelable covering 2 preferably comprises polyester with paper back or release agent. In a preferred embodiment, the peelable covering 2 of the adhesive bandage 7 comprises a pair of layers 2A and 2B which may optionally have an area of overlap. (Please refer to FIG. 2.) Preferably, in order to facilitate positioning of the wound binding layer 4 over the wound, a portion of one layer 2A overlaps a portion of the other layer 2B at a site above the wound binding layer 4. (Either layer 2A or layer 2B could be the upper layer. However, the overlap areas of the peelable covering 2 are referred to as "overlap area of layer 2A" and "overlapped area of layer 2B" for convenience.) Neither the overlap area of layer 2A nor the overlapped area of layer 2B is attached to the adhesive bandage 7. The overlap area of layer 2A and the overlapped area of layer 2B are actually not attached to any component of the bandage dressing system 10. The overlap area of layer 2A and the overlapped area of layer 2B are left free to allow the user to quickly and easily hold each of the layers 2A and 2B by, preferably, two fingers at any time. Each layer 2A and 2B of the peelable covering 2 is finger-tearable in a predetermined transverse direction, such that the direction of tear of one layer 2A is opposite to the direction of tear of the other layer 2B. With each layer 2A and 2B being finger-tearable in a predetermined transverse direction, the tear of tearable layers (i.e. the tear of the peelable cover 3 from the wound binding layer 4 and, eventually, the tear of the layers 2A and 2B of the peelable covering 2 from the adhesive bandage 7) and the attachment of attachable layers (i.e. the adhesive bandage 7, the wound binding layer 4 and the flexible layer 5) are facilitated. The tearable layers and attachable layers are arranged as clearly-identifiable, separate components.

The peelable cover 3 of the wound binding layer 4 preferably comprises a polyethylene film. The peelable cover 3 completely covers the wound binding layer 4 until the wound binding layer 4 is exposed upon removal of the peelable cover 3. The peelable cover 3 serves to prevent any contact of the wound binding layer 4 with the peelable layers 2A and 2B and with the air-tight or vacuum package 1 prior to the application of the wound binding layer 4 to the wound.

The wound binding layer 4 serves as a major contributor to the new and non-obvious features of the present invention. What has long been sought in the field of bandage systems, which the present invention offers, is a bandage dressing system 10 which is especially occlusive and adhesive, which provides an improved wound healing environment and which provides the convenience of an adhesive facing so that no tape is needed to hold it in place. Existing hydrocolloid absorbent adhesive wound binding layers dissolve in the presence of wound fluid unless changed frequently, leaving a wound bed which must be cleaned before the application of a fresh bandage dressing system. The particular wound binding layer 4 of the bandage dressing system 10 of the present invention does not dissolve. The wound binding layer 4 adheres to the skin and actually provides a relatively occlusive interface with the wound until there is a natural slough off of the wound binding layer 4 and of the flexible layer 5 from the wound. The preferred embodiment of the bandage dressing system 10 manages wound, secondary to the adhesive and occlusive wound binding layer 4.

The specific thickness of the wound binding layer 4 is relatively unimportant, but is preferably from approximately $1/32$ inches to $1/8$ inches. The wound binding layer 4 is prepared under aseptic conditions or alternatively sterilized after packing by a conventional procedure.

The ingredients of the wound binding layer 4 include a number of antibacterial agents. The wound binding layer 4 comprises cyanoacrylate, derivatives of cyanoacrylate, methylmethacrylate, methane sulfonic acid which serves as a preservative and fumed silica. Illustrative examples of suitable cyanoacrylates are: N-butyl-cyanoacrylate. In a preferred embodiment, the major component of the wound binding layer 4 is butyl-cyanoacrylate. According to many studies, cyanoacrylate has bacteriostatic activity. Cyanoacrylate inhibits the growth of the following bacteria: *Streptococcus pyogenes, Streptococcus mitis, Escherichia coli, Pseudomonas aeruginosa* and *Staphlococcus aureus*. Most of these bacteria are common skin pathogens. Methylmethacrylate is applied to modify the physical property and consistency of the wound binding layer 4 such that the bandage dressing system 10 is easier to handle and more consumer friendly. Preservatives, such as methane sulfonic acid, are used to increase the shelf life of the wound binding layer 4. Some candidates for future embodiments are bacitracin, neomycin sulfate, polymyxin B sulfate and lidocaine.

The composition of the wound binding layer 4 is preferably in the range of approximately: 88 percent to 98 percent of butyl-cyanoacrylate, 2 percent to 18 percent of methylmethacrylate, 0.5 percent to 2 percent of fumed silica and 5 parts per million to 30 parts per million of methane sulfonic acid. In addition, other ingredients, including but not limited to antibiotics and local anesthetics, may be used in the wound binding layer 4. Use of shorter side chains (for example, methyl or ethyl) for cyanoacrylates results in lower cure rate.

Since the mid-1960s, there have been medical interests in cyanoacrylates as a tissue-bonding agent. It may be interesting to note that cyanoacrylates products such as Krazy Glue (ethyl-cyanoacrylate) and Histoacryl (butyl-cyanoacrylate) have been used in many different medical studies. Experiments and tests have indicated that butyl-cyanoacrylate is more bio-compatible with human tissue than ethyl-cyanoacrylate is. However, all commercially available cyanoacrylate products are found to be without bacterial contamination and this sterility continues even after repeated usage by various patients from the same vial or container. Lack of bacterial contamination, even after repeated exposures, is a strong indication of the bacteriostatic action of cyanoacrylate.

Cyanoacrylate derivatives are differentiated by their side chains (methyl, ethyl, iso-butyl, butyl, hexyl etc.). Cyanoacrylates with longer side chains and increased purity have been found to be more bio-compatible and to have higher rates of polymerization (curing). The degradation products of cyanoacrylates are formaldehyde and the corresponding cyanoacetate. The formaldehyde will turn into carbon dioxide ($CO_2$) which will react with ammonium and turn into urea excreted in the urine and feces. According to radiotag studies of cyanoacrylate, there is no uptake of cyanoacrylate or any of its by-products into animal organs by any metabolic pathways. Therefore, the degradation of cyanoacrylate is complete without accumulations in human tissues.

Compounds comprising cyanoacrylates have been used as tissue-bonding agents in numerous medical studies. Such compounds were applied to a 3200 patient study regarding closing of minor surgical incisions, a 134 patient study regarding embolization of arterial and venous malformation in neurosurgery, a 135 patient study regarding closure of bronchopleural fistula in lungs and a 13 patient study regarding application of Teflon patches to close ruptured left ventricles in patients with cardiac tamponade. Cyanoacrylate compounds have also been applied for closing of sclera in eye surgery, for stopping active ulcers from bleeding, for facial laceration closures of pediatric patients, for split thickness skin graft placements and for hair transplantation to decrease cobblestoning which is an unsightly result of graft elevation in recipient site after hair transplantation.

In a double-blind study on closures of 81 pediatric facial surgeries, closures by cyanoacrylate were compared to closures by sutures. At a three-month follow-up, the wound closures were rated by the plastic surgeons. No significant differences were found between results of closures by cyanoacrylate versus results of closures by sutures.

However, in numerous studies, it has been found that, in comparison to sutures, cyanoacrylate tissue adhesives are more advantageous for surface cutaneous wound closures. The advantages result from lack of any need for local anesthetics and for suture removal, greater safety and reliability and lower costs. Although more studies are needed, cyanoacrylate closures may even result in a decrease of keloid formation (i.e. hypertrophic scars which invade nearby tissue) when compared to results from closures by sutures.

In studies where wound closures by cyanoacrylate were compared with wound closures by silk sutures, more severe inflammatory response and giant cell reaction resulted from silk suture closures than from cyanoacrylate closures. Wound closures by percutaneous sutures were found to damage host defenses and invite growth of bacteria to a level significantly greater than wound closures by cyanoacrylate do.

Based on the results of such tests, experiments and studies on the effect of cyanoacrylate and its derivatives on wounds, butyl-cyanoacrylate is a preferred candidate for serving as the major component of the wound binding layer 4.

The wound binding layer 4 and the flexible layer 5 minimize contaminations. The flexible layer 5 is impermeable to water. Secondary to its chemical composition, the wound binding layer 4 retards bacterial growth. (Further studies are needed to determine whether the wound binding layer 4 is bactericidal or not.) The adhesive flexible layer 5 and the wound binding layer 4 serve as an impervious layer in the initial wound healing phase, preventing passage of contaminants and moisture from external sources to the wound. By comprising a continuous layer without any holes, the flexible layer 5 is capable of serving as an occlusive layer. Upon application of the bandage dressing system 10 to the wound, the edges of the flexible layer 5 are all sealed. The seal formed over the wound helps reduce external contamination and external fluid from coming in contact with the wound during the initial wound healing phase of the wound. According to studies, fresh clean uncomplicated wounds have no resistance to infection resulting from surface contamination in approximately the initial six hours following the injury. During an initial healing phase which lasts approximately five days, collagen formation and epithelial coverage of the wound occur. A resistance to infection is gradually built up secondary to the initial phase of healing. The bandage dressing system 10 serves to reduce the complication of the wound from external contaminants and external fluid by creating a temporary waterproof seal that covers the wound. As a result, the initial healing phase of the wound can take place in a clean environment with minimal external disturbances. Usually, by day five of the initial healing phase, the uncomplicated wound has the same resistance to infection as intact skin does. It is at the time of the initial healing phase that the seal gradually sloughs off.

A wide range of polymeric material, consisting of polyolefins, polyamides, polyethylenes, polypropylenes, polyurethanes, polyesters, polysiloxane, acrylic, vinyl or any other suitable material, can be used for the flexible layer 5. Flexible layers 5 of polyolefins or polyamides are preferably made of non-homogeneous blends of polyolefins or polyamides, respectively. In a most preferred embodiment, polyethylenes, which are impermeable to water, serve as a component of the flexible layer 5. High molecular weight polyethylenes, which are used in many plastic products like plastic containers and toys, are especially preferred. Polymeric films such as polypropylenes, polyurethanes, polyesters and vinyl can be used to provide an occlusive feature to the flexible layer 5.

The thickness of the flexible layer 5 is in the range of approximately $1/128$ inches to $1/8$ inches. It maintains its physical integrity under normal handling conditions, is not soiled due to its chemical inertness and low surface tension, does not physically or chemically degrade (i.e. has relatively long shelf-life) and its chemical and physical properties are not adversely affected by changes in temperature ranging from approximately 20° F. to 180° F. (More testings should be performed in order to confirm this estimate of temperature range.)

Another goal of the present invention is designing a bandage dressing system 10 that is in all respects non-irritating to the patient. The adhesive bandage 7 is structured to allow the removal of the adhesive bandage 7 as easily in a transverse or longitudinal direction as the removal of the peelable covering 2 of the adhesive bandage 7 is. In a preferred embodiment, the adhesive bandage 7 is a single leaf which is peeled off from one end to the other. Once the tear of the adhesive bandage 7 is initiated, the removal of the adhesive bandage 7 requires minimal effort. The peeling off of the peelable covering 2 yields an exposed area of the adhesive bandage 7 that is neither covered by the flexible layer 5 nor by the wound binding layer 4. This exposed area of the adhesive bandage 7 is preferably composed of two sections 7A and 7B which correspond to layers 2A and 2B of the peelable covering 2. Upon removal of layer 2A of the peelable covering 2, section 7A of the adhesive bandage 7 is exposed. Upon removal of layer 2B of the peelable covering 2, section 7B of the adhesive bandage 7 is exposed. A remaining section of the adhesive bandage 7 is attached to and is covered by the flexible layer 5, as shown in FIG. 1.

In a preferred embodiment, the adhesive bandage 7 consists of a polymer blend of an ethylene/vinyl acetate, microporous paper or other suitable compounds. The adhesive bandage 7 that is made of microporous paper can be dissolved and washed away by water over time, leaving the water-tight seal formed by the flexible layer 5 and the wound binding layer 4 over the wound.

The peelable attachment 6 is used to attach a section of the adhesive bandage 7 to the flexible layer 5 and another section 7A,7B of the adhesive bandage 7 to the peelable covering 2. (Please refer to FIG. 2.) The peelable attachment 6 serves as a release coating, facilitating separation of the adhesive bandage 7 from the flexible layer 5 and from the peelable covering 2. A coating of a pressure-sensitive adhesive, preferably an acrylic pressure-sensitive adhesive or a water-based pressure-sensitive adhesive, is used as the peelable attachment 6.

Therefore, as indicated above, with the peelable attachment 6 attaching part of the adhesive bandage 7 to the peelable covering 2 and part of the adhesive bandage 7 to the flexible layer 5 which lies under the wound binding layer 4 that is covered by the peelable cover 3, the first embodiment of the bandage dressing system 10 is positioned and marketed as one unified system in an air-tight or vacuum package 1. For the second embodiment, with the peelable cover 3 covering the wound binding layer 4 that lies over the flexible layer 5, the bandage dressing system 10 is positioned and marketed as one unified system in an air-tight or vacuum package 1.

The bandage dressing system 10 is intended to be easily handled and used. The wound should be first cleaned with soap and water or with other disinfectants like alcohol or hydrogen peroxide. The wound should be relatively dry with minimal bleeding when the bandage dressing system 10 is to be applied. To apply the bandage dressing system 10, the air-tight or vacuum package 1 is broken. Upon removal of the bandage dressing system 10 from the air-tight or vacuum package 1, the peelable covering 2 of the adhesive bandage 7 is removed.

The layers 2A and 2B of the peelable covering 2 can be easily grasped at the site of their overlap. A portion of the overlap area of layer 2A is grasped between a finger and the thumb of one hand on one side of a desired separation line and layer 2A is removed from the adhesive bandage 7. Then, with one hand's thumb and index finger holding the exposed section 7A of the adhesive bandage 7, the other layer 2B is removed by the thumb and index finger of the other hand. As the layers 2A and 2B are removed, the peelable cover 3 of the wound binding layer 4 and an area of the adhesive bandage 7 that is neither covered by the flexible layer 5 nor by the wound binding layer 4 are exposed.

Upon holding one of the exposed sections 7A or 7B of the adhesive bandage 7 between the thumb and a finger of one hand, the peelable cover 3 of the wound binding layer 4 is removed with the thumb and a finger of the other hand. Removal of the peelable cover 3 exposes the wound binding layer 4 to the air and the moisture in the air, even if for a very short period of time. The wound binding layer 4 and, thus, the flexible layer 5 are then positioned over the wound and stabilized by positioning each section 7A and 7B of the adhesive bandage 7 on the corresponding side of the wound. It is advisable to use minimal pressure while applying the wound binding layer 4 over the wound. If excessive force is used, some components of the wound binding layer 4 may leak out around the edges of the flexible layer 5 before the wound binding layer 4 is cured to the wound. The exposed sections 7A and 7B of the adhesive bandage 7, that were previously covered by layers 2A and 2B of the peelable covering 2 respectively, are used to stabilize the wound binding layer 4 by manipulating, with minimal fingering of, the wound binding layer 4 and the flexible layer 5 over and around the wound when bringing the exposed sections 7A and 7B into contact with the skin.

The exposed sections 7A and 7B of the adhesive bandage 7 that are originally covered by layers 2A and 2B of the peelable covering 2 are then secured to the sides of the wound until the wound binding layer 4 is cured over and around the wound, while the other section of the adhesive bandage 7 remains attached to the flexible layer 5. It takes about one minute to ten minutes for the wound binding layer 4 to cure over the wound. Upon formation of the waterproof seal, which consists of the wound binding layer 4 and the flexible layer 5, the adhesive bandage 7 is removed at any desirable time. As a guideline, the edges of the flexible layer 5 can be checked after about five to ten minutes from the initial application of the wound binding layer 4 to the wound site. If the edges of the flexible layer 5 appear to be stable and non-mobile, the adhesive bandage 7 may be removed. When the seal formation of the flexible layer 5 and the wound binding layer 4 over the wound is completed, the adhesive bandage 7 can be either removed as one piece or washed away gradually in portions. (The amount of hair in the area adjacent to the wound may affect the seal formation and may provide some discomfort if the adhesive bandage 7 is removed as one piece.) The simple removal of the adhesive bandage 7 upon formation of the seal is due to the fact that the strength of the seal over the wound by the wound binding layer 4 and by the flexible layer 5 is much greater than the strength of the attachment by a pressure-sensitive adhesive, serving as the peelable attachment 6, between the flexible layer 5 and the adhesive bandage 7 and between the adhesive bandage 7 and the corresponding wound-site area.

Butyl-cyanoacrylate plays an essential role in the function of the bandage dressing system 10. When the bandage dressing system 10 is opened and the peelable cover 3 of the wound binding layer 4 is removed, the wound binding layer 4 is exposed to the moisture in the air. Next, when the wound binding layer 4 is positioned over the wound, the wound binding layer 4 is exposed to both the moisture in the wound and to tissue proteins in the wound. Once the butyl-cyanoacrylate comes into contact with the moisture in the air, moisture in the wound and nitrogen molecules of tissue proteins in the wound, the butyl-cyanoacrylate undergoes anionic polymerization. The anionic polymerization of the butyl-cyanoacrylate causes its carbon-carbon double bond to open up and, thus, the butyl-cyanoacrylate cures and becomes impermeable to water. (Although no studies have proven the steps involved in curing and causing the impermeability of butyl-cyanoacrylate to water, anionic polymerization is an accepted explanation for the cause of curing of butyl-cyanoacrylate.) As a result, the exposure of the wound binding layer 4 to the moisture in the air eventually leads to the curing of the wound binding layer 4 to the wound and to the flexible layer 5, resulting in the formation of a seal over the wound. Topped with an occlusive outer layer, the wound binding layer 4 provides the barrier against external contaminants and moisture.

Upon removal of the adhesive bandage 7 as one piece or gradually in portions, the flexible layer 5 and the wound binding layer 4 of the bandage dressing system 10 remain on the wound and keep the wound dry and water proof. After the initial stage of the wound healing has taken place, usually within a period of about five to ten days, the wound binding layer 4 and the flexible layer 5 of the bandage dressing system 10 slough off naturally and gradually from the wound. It should also be noted that the wound binding layer 4 and the flexible layer 5 may be peeled off at any desired time. The sloughing off process takes place secondary to daily activities such as washing hands and bathing, to excretion of internal moisture and perspiration from the wound itself and to possible digestion of the butyl-cyanoacrylate from the wound binding layer 4 by tissue enzymes. (More studies are needed to demonstrate the digestion of the butyl-cyanoacrylate from the wound binding layer 4 by tissue enzymes.) The moisture from daily activities slowly passes by capillary action around the edges of the wound and between the wound binding layer 4 and the wound. Meanwhile, the internal moisture and perspiration from the wound itself helps to promote the sloughing off process.

For some types of wounds (e.g. for wounds that are in certain locations of the body with abundant hair), it is preferable to avoid the attachment of the adhesive bandage 7 to the wound site. When the flexible layer 5 and the wound binding layer 4 are positioned over and around the wound, the adhesive bandage 7 is removed from the flexible layer 5 without contacting the wound site. Thus, the pain and discomfort of removing the adhesive bandage 7 as one piece, several minutes later after the wound binding layer 4 is cured, is avoided. Of course, the adhesive bandage 7 of microporous paper can be gradually washed away in portions by water without causing any pain and discomfort.

The present bandage dressing system 10 surpasses the effectiveness of existing bandage dressing systems that are available in the market. The present invention is economical, has stable shelf life, has small bulk, resists tearing, resists soiling, has constant properties in a range of temperatures and humidities encountered in use, is compatible with medicaments, is neither toxic nor incompatible to human tissue, conforms to anatomical contours, supplies mechanical protection to the wound, does not shed loose material into the wound and protects against secondary infection. Despite all its advantages, the bandage dressing system 10 is recommended to be used for minor wounds, namely cuts and abrasions.

Certain objects are set forth above and made apparent from the foregoing description, drawings and examples. However, since certain changes may be made in the above description, drawings and examples without departing from the scope of the invention, it is intended that all matters contained in the foregoing description, drawings and examples shall be interpreted as illustrative only of the principles of the invention and not in a limiting sense. With respect to the above description and examples then, it is to be realized that any descriptions, drawings and examples deemed readily apparent and obvious to one skilled in the art and all equivalent relationships to those stated in the examples and described in the specification or illustrated in the drawings are intended to be encompassed by the present invention.

Further, since numerous modifications and changes will readily occur to those skilled in the art, it is not desired to limit the invention to the exact construction and operation shown and described, and accordingly, all suitable modifications and equivalents may be resorted to, falling within the scope of the invention. It is also to be understood that the following claims are intended to cover all of the generic and specific features of the invention herein described, and all statements of the scope of the invention which, as a matter of language, might be said to fall in between.

What is claimed as invention is:

1. A bandage dressing system, which is stored in an air-tight or vacuum package, consists of a number of layers including an uppermost layer and a bottommost layer and comprises:
   (a) a wound binding layer that comprises one or more cyanoacrylates;
   (b) a flexible layer that is positioned under the wound binding layer;
   (c) a peelable cover that is positioned over the wound binding layer;
   (d) an adhesive bandage that is the bottommost layer;
   (e) a peelable covering that is the uppermost layer; and
   (f) a peelable attachment that is positioned over the adhesive bandage and that attaches one section of the adhesive bandage to the flexible layer and that attaches another section of the adhesive bandage to the peelable covering;
   such that upon removal of the peelable covering and the peelable cover, the wound binding layer is positioned over the wound and the section of the adhesive bandage that was attached to the peelable covering is secured to the sides of the wound.

2. The bandage dressing system according to claim 1, wherein the air-tight or vacuum package is made of aluminum or paper polyethylene.

3. The bandage dressing system according to claim 1, wherein cyanoacrylates and derivatives of cyanoacrylates are major components of the wound binding layer.

4. The bandage dressing system according to claim 3, wherein butyl-cyanoacrylate is the major component of the wound binding layer.

5. The bandage dressing system according to claim 3, wherein the wound binding layer further comprises metylmethacrylate, methane sulfonic acid and fumed silica.

6. The bandage dressing system according to claim 1, wherein the flexible is a continuous, non-porous layer.

7. The bandage dressing system according to claim 1, wherein the flexible consists of polyolefins, polyamides, polyethylenes, polypropylenes, polyurethanes, polyesters, polysiloxane, acrylic or vinyl.

8. The bandage dressing system according to claim 1, wherein the flexible layer is between approximately 1/128 and 1/8 inches thick.

9. The bandage dressing system according to claim 1, wherein the peelable cover comprises a polyethylene film.

10. The bandage dressing system according to claim 1, wherein the peelable attachment comprises a water-based, pressure-sensitive adhesive.

11. A bandage dressing system, which is stored in an air-tight or vacuum package, comprises:
    (a) a wound binding layer that is positioned over the wound and that comprises one or more cyanoacrylates;
    (b) a flexible layer that is positioned under the wound binding layer and that is the bottommost layer; and
    (c) a peelable cover that is positioned over the wound binding layer and that is the uppermost layer.

12. The bandage dressing system according to claim 11, wherein the air-tight or vacuum package is made of aluminum or paper polyethylene.

13. The bandage dressing system according to claim 11, wherein cyanoacrylates and derivatives of cyanoacrylates are major components of the wound binding layer.

14. The bandage dressing system according to claim 13, wherein butyl-cyanoacrylate is the major component of the wound binding layer.

15. The bandage dressing system according to claim 13, wherein the wound binding layer further comprises methylmethacrylate, methane sulfonic acid and fumed silica.

16. The bandage dressing system according to claim 11, wherein the flexible layer is a continuous, non-porous layer.

17. The bandage dressing system according to claim 11, wherein the flexible layer consists of polyolefins, polyamides, polyethylenes, polypropylenes, polyurethanes, polyesters, polysiloxane, acrylic or vinyl.

18. The bandage dressing system according to claim 11, wherein the flexible layer is between approximately 1/128 and 1/8 inches thick.

19. The bandage dressing system according to claim 11, wherein the peelable cover comprises a polyethylene film.

20. A method of treating a wound by using a bandage dressing system, that is stored in an air-tight or vacuum package, that consists of a number of layers including an uppermost layer and a bottommost layer and that comprises a wound binding layer that comprises one or more cyanoacrylates, a flexible layer that is positioned under the wound binding layer, a peelable cover that is positioned over the wound binding layer, an adhesive bandage that is the bottommost layer, a peelable covering that is the uppermost layer and a peelable attachment that is positioned over the adhesive bandage and that attaches one section of the adhesive bandage to the flexible layer and that attaches another section of the adhesive bandage to the peelable covering, said method comprising:
    (a) removing the bandage dressing system from the air-tight or vacuum package;
    (b) removing the peelable covering from the adhesive bandage;
    (c) removing the peelable cover from the wound binding layer;
    (d) positioning the wound binding layer and the flexible layer over the wound, with the wound binding layer being cured over the wound, while securing the adhesive bandage to site of the wound; and (e) removing, either in one piece or gradually in sections, the adhesive bandage upon formation of a water tight seal by the flexible layer and by the wound binding layer over the wound, with the peelable attachment serving as a release coating such that the strength of the seal over the wound by the wound binding layer and by the flexible layer being considerably greater then the strength of the attachment between the flexible layer and the adhesive bandage and between the adhesive bandage and the site of the wound, thus facilitating separation of the adhesive bandage from the flexible layer and from the wound;

whereby the flexible layer and the wound binding layer, by forming a waterproof seal around and over the wound, provide a barrier for the wound against contamination and external moisture and reduce infection such that the initial wound healing phase takes place in a clean environment with minimal external disturbances; and whereby when initial wound healing phase is basically complete, the wound binding layer and the flexible layer slough off naturally and gradually from the wound.

21. The method of treating a wound according to claim 20, wherein the adhesive bandage is removed about one minute to ten minutes after the application of the wound binding layer and the flexible layer to the wound.

22. The method of treating a wound according to claim 20, wherein when the wound binding layer and the flexible layer are positioned over the wound, the adhesive bandage is removed without contacting the wound site.

23. The method of treating a wound according to claim 20, wherein the wound binding layer and the flexible layer slough off naturally and gradually from the wound about five to ten days following the application of the wound binding layer and the flexible layer to the wound.

24. A method of treating a wound by using a bandage dressing system, which is stored in an air-tight or vacuum package and which comprises a wound binding layer that comprises one or more cyanoacrylates, a flexible layer that is positioned under the wound binding layer and that is the bottommost layer and a peelable cover that is positioned over the wound binding layer and that is the uppermost layer, said method comprising:

(a) removing the bandage dressing system from the air-tight or vacuum package;

(b) removing the peelable cover from the wound binding layer; and (c) positioning the wound binding layer and the flexible layer over the wound, with the wound binding layer being cured over the wound;

whereby the flexible layer and the wound binding layer, by forming a waterproof seal over and around the wound, provide a barrier for the wound against contamination and external moisture and reduce infection such that the initial wound healing phase can take place in a clean environment with minimal external disturbances; and whereby when initial wound healing phase is basically complete, the wound binding layer and the flexible layer slough off naturally and gradually from the wound.

25. The method of treating a wound according to claim 24, wherein the wound binding layer and the flexible layer slough off naturally and gradually from the wound about five to ten days following the application of the wound binding layer and the flexible to the wound.

26. A method of treating a wound comprising:

(a) applying to the wound a bandage dressing system removed from an air-tight or vacuum package, said bandage dressing system comprising a wound binding layer that comprises one or more cyanoacrylates, a flexible layer that is positioned under the wound binding layer, a number of peelable coverings that are positioned over the wound binding layer and an adhesive bandage that is the bottommost layer;

(b) upon removing any coverings that are in contact with the wound binding layer in order to expose one side of the wound binding layer that comes in direct contact with the wound, positioning the wound binding layer, the flexible layer and the adhesive bandage over the wound; and (c) removing, either as one piece or gradually in sections, the adhesive bandage upon formation of a water tight seal by the flexible layer and by the wound binding layer over and around the wound;

whereby the flexible layer and the wound binding layer, by forming a waterproof seal over and around the wound, provide a barrier for the wound against contamination and external moisture and reduce infection such that the initial wound healing phase takes place in a clean environment with minimal external disturbances; and whereby when initial wound healing phase is basically complete, the wound binding layer and the flexible layer slough off naturally and gradually from the wound.

27. The method of treating a wound according to claim 26, wherein the adhesive bandage is removed about one minute to ten minutes after the application of the wound binding layer and the flexible layer to the wound.

28. The method of treating a wound according to claim 26, wherein when the wound binding layer and the flexible layer are positioned over the wound, the adhesive bandage is removed without contacting the wound site.

29. The method of treating a wound according to claim 26, wherein the wound binding layer and the flexible layer slough off naturally and gradually from the wound about five to ten days following the application of the wound binding layer and the flexible layer to the wound.

30. A method of treating a wound comprising:

(a) applying to the wound a bandage dressing system removed from an air-tight or vacuum package, said bandage dressing system comprising a wound binding layer that comprises one or more cyanoacrylates, a flexible layer that is positioned under the wound binding layer and a number of peelable coverings that are positioned over the wound binding layer; and (b) upon removing any coverings that are in contact with the wound binding layer in order to expose one side of the wound binding layer that comes in direct contact with the wound, positioning the wound binding layer and the flexible layer over the wound;

whereby the flexible layer and the wound binding layer, by forming a waterproof seal over and around the wound, provide a barrier for the wound against contamination and external moisture and reduce infection such that the initial wound healing phase takes place in a clean environment with minimal external disturbances; and whereby when initial wound healing phase is basically complete, the wound binding layer and the flexible layer slough off naturally and gradually from the wound.

31. The method of treating a wound according to claim 30, wherein the wound binding layer and the flexible layer slough off naturally and gradually from the wound about five to ten days following the application of the wound binding layer and the flexible layer to the wound.

* * * * *

UNITED STATES PATENT AND TRADEMARK OFFICE
CERTIFICATE OF CORRECTION

PATENT NO. : 5,780,048
DATED : July 14, 1998
INVENTOR(S) : Chung Chih Lee

It is certified that error appears in the above-identified patent and that said Letters Patent is hereby corrected as shown below:

In claim 6, line 2, after "flexible" insert -- layer --.

In claim 7, line 2, after "flexible" insert -- layer --.

In claim 25, line 5, after "flexible" insert -- layer --.

Also, the address of the inventor is in "Bellaire, Tex.", not "Bellaine, Tex.".

Signed and Sealed this

Ninth Day of March, 1999

*Attest:*

Q. TODD DICKINSON

*Attesting Officer*  *Acting Commissioner of Patents and Trademarks*